(12) United States Patent
Fisher et al.

(10) Patent No.: US 6,484,056 B2
(45) Date of Patent: Nov. 19, 2002

(54) SYSTEM AND METHOD OF GENERATING A HIGH EFFICIENCY BIPHASIC DEFIBRILLATION WAVEFORM FOR USE IN AN IMPLANTABLE CARDIOVERTER/ DEFIBRILLATOR (ICD)

(75) Inventors: Matthew G. Fisher, Ithaca, NY (US); Gabriel A. Mouchawar, Newhall, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 96 days.

(21) Appl. No.: 09/803,271

(22) Filed: Mar. 9, 2001

(65) Prior Publication Data

US 2001/0031992 A1 Oct. 18, 2001

Related U.S. Application Data

(63) Continuation-in-part of application No. 09/073,394, filed on May 5, 1998, now Pat. No. 6,233,483
(60) Provisional application No. 60/046,610, filed on May 14, 1997.

(51) Int. Cl.$^7$ ................................................. A61N 1/39
(52) U.S. Cl. ............................................. 607/5; 607/74
(58) Field of Search ............................... 607/4, 5, 74, 6, 607/7, 68

(56) References Cited

U.S. PATENT DOCUMENTS

| 4,637,397 A | * | 1/1987 | Jones et al. ..................... 607/5 |
| 4,850,357 A |   | 7/1989 | Bach, Jr. ................. 128/419 D |
| 5,083,562 A |   | 1/1992 | De Coriolis et al. ..... 128/419 D |
| 5,199,429 A |   | 4/1993 | Kroll et al. .................. 128/419 |
| 5,370,663 A | * | 12/1994 | Lin ............................. 607/36 |
| 5,385,575 A | * | 1/1995 | Adams .......................... 607/5 |
| 5,395,395 A |   | 3/1995 | Hedberg ........................ 607/7 |
| 5,411,525 A |   | 5/1995 | Swanson et al. ................ 607/5 |
| 5,507,781 A | * | 4/1996 | Kroll et al. .................... 607/74 |
| 5,658,321 A | * | 8/1997 | Fayram et al. ................ 607/36 |
| 5,800,462 A | * | 9/1998 | Lopin et al. .................... 607/7 |
| 5,833,712 A | * | 11/1998 | Kroll et al. .................... 607/7 |
| 5,908,443 A | * | 6/1999 | Brewer et al. ................. 607/5 |
| 5,913,877 A | * | 6/1999 | Kroll et al. .................... 607/5 |
| 6,041,254 A |   | 3/2000 | Sullivan et al. ................ 607/5 |

FOREIGN PATENT DOCUMENTS

AU          0272021     *  7/1964    ..................... 607/5

OTHER PUBLICATIONS

Walcott, Gregory P., et al., Choosing the Optimal Monophasic and Biphasic Waveforms for Ventricular Defibrillation, Journal of Cardiovascular Electrophysiology, vol. 6, No. 9, pp: 737–750 (Sep. 1995).

Pearce, J.A., et al., Myocardial Stimulation with Ultrashort Duration Current Pulses, PACE, vol. 5, pp: 52–58 (Jan.–Feb. 1982).

Kroll, Mark W., A Minimal Model of the Single Capacitor Biphasic Defibrillation Waveform, PACE, vol. 17, Part 1, pp: 1782–1792 (Nov. 1994.

(List continued on next page.)

*Primary Examiner*—Kennedy Schaetzle

(57) ABSTRACT

In an ICD, a highly efficient biphasic defibrillation pulse is generated by switching at least two charged capacitors from a parallel connection to various combinations of a parallel/ series connection or a series connection during the first phase of the defibrillation pulse. Such mid-stream parallel/ series connection changes of the capacitors and steps up the voltage applied to the cardiac tissue during the first phase. A stepped-up voltage during the first phase, in turn, gives an extra boost to, and thereby forces additional charge (current) into, the cardiac tissue cells, and thereby transfers more charge to the membrane of the excitable cardiac cell than if the capacitors were continuously discharged in series. Phase reversal is timed with the cell membrane reaching its maximum value at the end of the first phase.

18 Claims, 10 Drawing Sheets

OTHER PUBLICATIONS

Blair, H.A., On the Intensity–Time Relations for Stimulation By Electric Currents. I, Journal of General Physiology, vol. 15, No. 6, pp: 709–729 (Jul. 20, 1932).

Blair, H.A., On the Intensity–Time Relations for Stimulation by Electric Currents. II, Journal of General Physiology, vol. 15 No. 6, pp: 731–755 (Jul. 20, 1932).

* cited by examiner

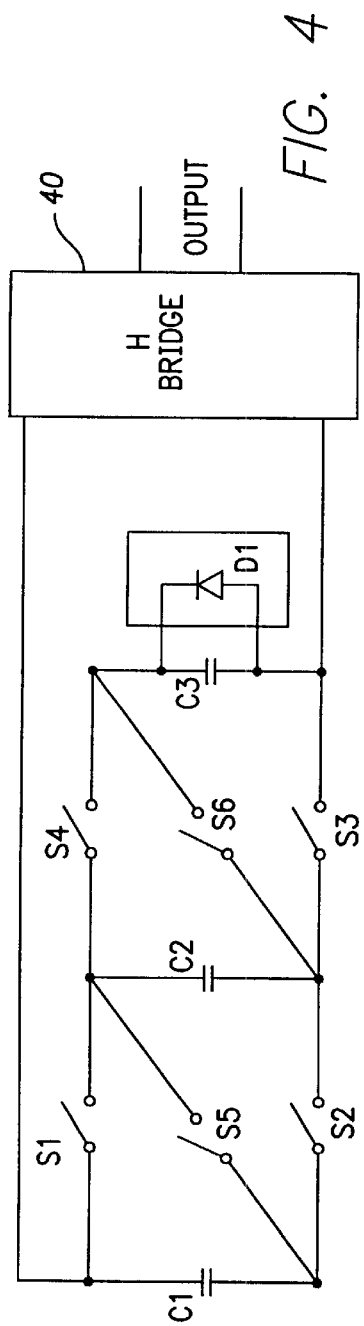
FIG. 4
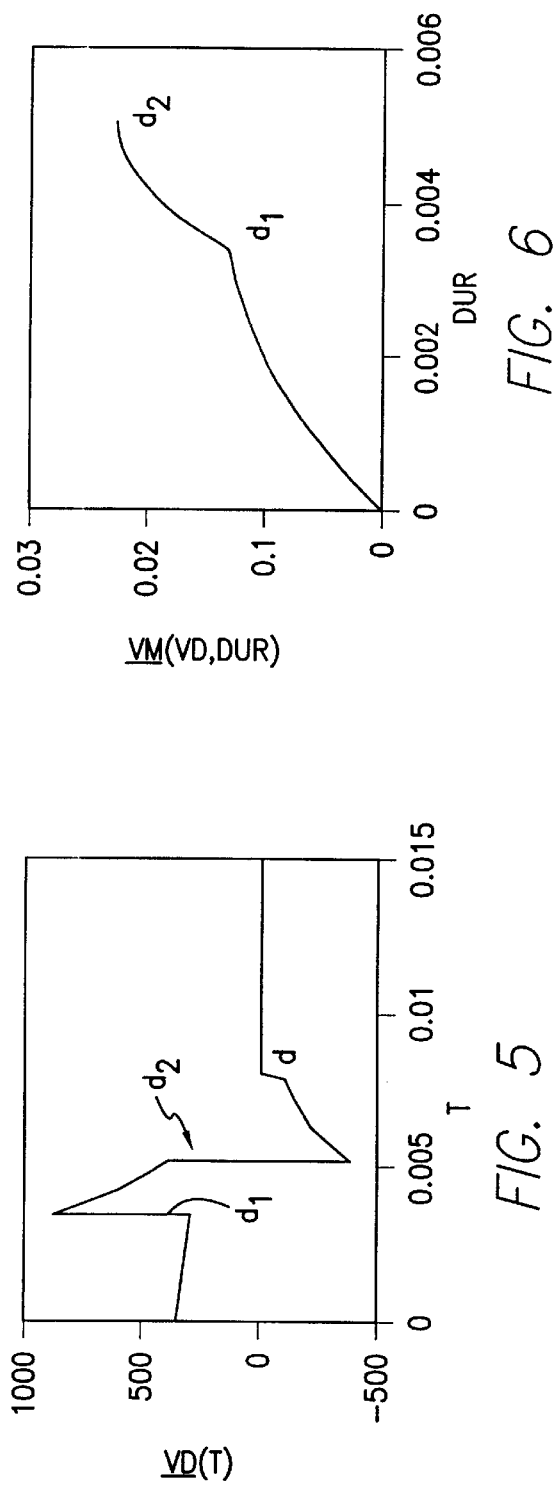
FIG. 6
FIG. 5

FIG. 15

| $\tau_m$ 2 ms | | | $R_S$ [ohms] | | | |
|---|---|---|---|---|---|---|
| | $d_1^{opt}$[ms] / $d_2^{opt}$[ms] | $c_A(=c_B)[\mu F]$ | 30 | 50 | 70 | 90 |
| | | 30 | 1.286 | 1.508 | 1.640 | 1.729 |
| | | | 0.422 | 0.647 | 0.842 | 1.014 |
| | | 60 | 1.581 | 1.763 | 1.862 | 1.923 |
| | | | 0.747 | 1.094 | 1.377 | 1.618 |
| | | 90 | 1.729 | 1.879 | 1.956 | 2.003 |
| | | | 1.014 | 1.441 | 1.778 | 2.058 |

FIG. 16

| $\tau_m$ 3 ms | | | $R_S$ [ohms] | | | |
|---|---|---|---|---|---|---|
| | $d_1^{opt}$[ms] / $d_2^{opt}$[ms] | $c_A(=c_B)[\mu F]$ | 30 | 50 | 70 | 90 |
| | | 30 | 1.655 | 2.000 | 2.219 | 2.372 |
| | | | 0.443 | 0.693 | 0.918 | 1.121 |
| | | 60 | 2.120 | 2.433 | 2.612 | 2.728 |
| | | | 0.808 | 1.216 | 1.562 | 1.863 |
| | | 90 | 2.372 | 2.645 | 2.792 | 2.885 |
| | | | 1.121 | 1.641 | 2.066 | 2.427 |

FIG. 17

| $\tau_m$ 4 ms | | | $R_S$ [ohms] | | | |
|---|---|---|---|---|---|---|
| | $d_1^{opt}$[ms] / $d_2^{opt}$[ms] | $c_A(=c_B)[\mu F]$ | 30 | 50 | 70 | 90 |
| | | 30 | 1.950 | 2.408 | 2.710 | 2.928 |
| | | | 0.454 | 0.720 | 0.963 | 1.188 |
| | | 60 | 2.573 | 3.016 | 3.280 | 3.458 |
| | | | 0.844 | 1.294 | 1.683 | 2.029 |
| | | 90 | 2.928 | 3.331 | 3.557 | 3.704 |
| | | | 1.188 | 1.773 | 2.264 | 2.689 |

SYSTEM AND METHOD OF GENERATING A HIGH EFFICIENCY BIPHASIC DEFIBRILLATION WAVEFORM FOR USE IN AN IMPLANTABLE CARDIOVERTER/ DEFIBRILLATOR (ICD)

CROSS-REFERENCE TO RELATED APPLICATIONS

This application claims the benefit of U.S. patent application No. 09/073,394, filed May 5, 1998, now U.S. Pat. No. 6,233,483, which claims the benefit of U.S. Provisional Patent Application No. 60/046,610, filed May 14, 1997.

FIELD OF THE INVENTION

The present invention relates to implantable medical devices, and more particularly to an implantable cardioverter defibrillator (ICD) configured to provide a high efficiency defibrillation waveform.

BACKGROUND OF THE INVENTION

An ICD continues to be a relatively large device for implantation in the human body. The size of the ICD is primarily determined by the battery and capacitors used therein. The size of the battery (or batteries, in some instances) and capacitors, in turn, is determined by the shock energy requirements for a defibrillation pulse. Thus, a design approach which reduces the energy requirements for defibrillation results in a direct reduction in the overall ICD size.

In existing ICD devices, the defibrillation waveform or pulse used to deliver a defibrillation shock to the heart is generated by first charging the equivalent of a single capacitor (most ICDs use two capacitors connected in series to function as a single capacitor, thereby reducing the working voltage requirements for each capacitor of the series stack, as explained below) to a desired charge level (voltage) and then discharging the single capacitor through the cardiac tissue for a prescribed period of time during a first or positive phase of the defibrillation waveform, and then reversing the polarity of the discharge for a second prescribed period of time during a second or negative phase of the defibrillation waveform, thereby producing a biphasic stimulation pulse or waveform. It should be noted that in this context the term "single capacitor" is used to refer to a single capacitance, which may be, and usually is obtained by a hardwired connection of two capacitors in series such that the two series capacitors always function and act as though they were a single capacitor. (Two capacitors are connected in series in this manner in order to achieve a higher working voltage for the series-connected capacitor. That is, when two capacitors are connected in series, and each has a working voltage of, e.g., 375 volts (V), then the overall or total working voltage of the series combination becomes 750 V.)

The purpose of applying a defibrillation shock to the heart is to shock the heart out of a state of fibrillation, or other non-functional state, into a functional state where it may operate efficiently as a pump to pump blood through the body. To this end, the positive phase of the biphasic waveform is preferably a very high voltage that serves to synchronously capture as many heart membrane cells as possible. See, Kroll, "A minimum model of the signal capacitor biphasic waveform" Pace, November 1994. The negative phase of the biphasic waveform, in contrast, simply serves to remove the residual electrical charge from the membrane cells and bring the collective membrane voltage back to its original position or value. See, e.g., Kroll, supra; Walcott, et al., "Choosing The Optimal Monophasic and Biphasic Wave-Forms for Ventricular Defibrillation,", Journal of Cardiovascular Electrophysiology (September 1995). A biphasic pulse generator of the type used in an ICD device is shown, e.g., in U.S. Pat. Nos. 4,850,357, issued to Bach, Jr.; and 5,083,562, issued to de Coriolis et al.

When a voltage shock is first applied to a membrane cell, the membrane does not respond to the shock immediately. Rather, the cell response lags behind the applied voltage. This time lag is more or less predictable in accordance with the Blair membrane model. See, e.g., Blair, "On the intensity-time relations for stimulation by electric currents. I" J. Gen Physiol., Vol. 15, pp. 709–729 (1932), and Blair, "On the intensity time relations for stimulation by electric currents. II", J. Gen Physiol., Vol. 15, pp. 731–755 (1932); Pearce et al., "Myocardial stimulation with ultrashort duration current pulses," PACE, Vol. 5, pp. 52–58 (1982). When the applied voltage comprises a biphasic pulse having a constant voltage level for the duration of the positive phase (a condition achievable only when the voltage originates from an ideal battery), the membrane cell response to the positive phase reaches a peak (i.e., is at an optimum level) at the trailing edge of the positive phase. Unfortunately, when the applied voltage originates from a charged capacitor, as is the case for an ICD device, the applied voltage waveform does not remain at a constant voltage level, but rather has a significant "tilt" or discharge slope associated therewith. Such tilt or slope causes the peak membrane cell response to occur at some point prior to the trailing edge of the positive phase, which is less than optimum. What is needed, therefore, is a way to optimize the applied voltage waveform so that a maximum membrane cell response occurs coincident with, or nearly coincident with, the trailing edge of the positive phase.

It is known in the art to switch the capacitors of an ICD from a parallel configuration during the positive phase of a biphasic defibrillation pulse to a series configuration during the negative phase of the biphasic defibrillation pulse. See, e.g., U.S. Pat. Nos. 5,199,429 (FIG. 7A) and 5,411,525. While such action produces a defibrillation waveform having a somewhat different shape, i.e., a waveform having a leading edge voltage of the second or negative phase which is approximately twice the trailing edge voltage of the first or positive phase, such action does little to achieve a maximum cell membrane response coincident with the trailing edge of the first or positive phase.

It is also known in the art to sequentially switch capacitors in an ICD device in order to allow waveform "tailoring", e.g., prolong the positive phase duration by sequentially switching in a second charged capacitor as shown in FIG. 9 of U.S. Pat. No. 5,199,429, or by sequentially switching in second, third and fourth charged capacitors, as shown in FIG. 6C of U.S. Pat. No. 5,199,429. However, such "tailoring" still does not address the main concern of achieving a maximum cell membrane response coincident with the trailing edge of the positive phase.

It is thus evident that what is needed is a capacitor switching scheme and/or method for use within an ICD device which achieves a maximum cell membrane response near or coincident with the trailing edge of the positive phase.

It is also desirable to provide an ICD that is as small as possible. The limiting factor on ICD thickness is the diameter of the high-energy capacitors. As indicated above, current ICDs typically use two electrolytic capacitors. Current technology in electrolytic capacitors limits the stored voltage to about 370 V per capacitor. Therefore, the current approach is to use two large ($\geq 180\ \mu F$) capacitors to achieve the stored energy of $\geq 25J$ required for defibrillation. Therefore, the thickness of the ICD is determined by the diameter of the large ($\geq 180\ \mu F$) capacitors. There is thus a need for an ICD construction, which would permit the needed energy for defibrillation to be stored in the ICD, while allowing a thinner ICD thickness.

The present invention advantageously addresses the above and other needs.

SUMMARY OF INVENTION

The present invention generates a highly efficient first phase (which is usually a positive phase) of a biphasic defibrillation pulse by switching at least two charged capacitors, preferably three capacitors, from a parallel connection to a series connection during the first or positive phase of the defibrillation pulse. Such mid-stream parallel-to-series switch advantageously steps up the voltage applied to the cardiac tissue during the first phase. A stepped-up voltage during the first phase, in turn, gives an extra boost to, and thereby forces additional charge (current) into, the cardiac tissue cells, and thereby transfers more charge into the membrane of the excitable cardiac cell than would be transferred if the capacitors were continuously discharged in series.

Phase reversal, e.g., switching to a second or negative phase of the biphasic waveform) is timed to occur when the cell membrane voltage reaches its maximum value at the end of the first phase.

In accordance with one aspect of the invention, two capacitors are used within the ICD to produce a two-step waveform that outperforms the conventional one-step waveform. It will be shown that the two-step waveform requires a 15.6% lower leading edge, which may result in significantly less pain felt by the patient, and further translates into at 28.8% reduction in required stored energy. This reduction in leading edge amplitude and required stored energy is achieved by controlling the durations of the first and second steps in the two-step positive portion of the waveform.

In accordance with another aspect of the invention, three capacitors are used within the ICD in order to provide a thinner ICD. These three capacitors store the same energy as a two-capacitor ICD. These smaller capacitors have a smaller diameter and therefore the ICD can be made thinner.

Disadvantageously, using three capacitors instead of two creates its own set of problems that must be overcome by the present invention. Using three capacitors discharged in series results in: (a) high peak voltages (generally the peak voltage can be three times 370 V or 1110 V); and (b) a small discharge time constant, since the effective capacitance is that of a single capacitor divided by three (or 40 $\mu F$ if 120 $\mu F$ capacitors are used), resulting in a mismatch between the discharge ($\tau = R^*C$, with $R \approx 50\Omega$) and tissue ($\tau_m \approx 3$ ms) time constants. Advantageously, the present invention addresses both of these concerns.

In accordance with another aspect of the invention, the capacitors of the ICD are reconfigured from a parallel configuration to a series configuration during the positive portion of the defibrillation pulse. While this concept may be used effectively with a two-capacitor ICD, it is preferred for purposes of the present invention that at least three capacitors be used, thereby allowing the ICD to be somewhat thinner that it otherwise could be.

It is therefore a feature of the present invention to provide an ICD that generates a highly efficient stimulation waveform that transfers more charge to the membrane of an excitable cardiac cell than has heretofore been possible using conventional, series-discharge configurations.

It is a further feature of the invention to provide an ICD design that results in a thinner ICD than has heretofore been possible using a conventional two-capacitor ICDs.

BRIEF DESCRIPTION OF THE DRAWINGS

The above and other aspects, features, and advantages of the present invention will be more apparent from the following more particular description thereof, presented in conjunction with the following drawings, wherein:

FIG. 4 is a simplified schematic diagram of a three-capacitor ICD made in accordance with the invention;

FIG. 5 illustrates one type of defibrillation waveform that may be generated using the ICD of FIG. 4;

FIG. 6 depicts the excitable cardiac membrane response during phase 1 (positive phase) to the waveform of FIG. 5;

FIGS. 15, 16 and 17 illustrate how the optimal values for $d_1$ and $d_2$, tissue resistance ($R_S$) and tissue time constants ($\tau_m$);

DETAILED DESCRIPTION OF THE INVENTION

The following description is of the best mode currently contemplated for practicing the invention.

The basic concept of the invention relating to forming an efficient defibrillation waveform can be practiced with two or more capacitors within the ICD. A preferred number of capacitors is three. However, the basic concept will first be explained in the context of a two-capacitor ICD.

Figure 1:
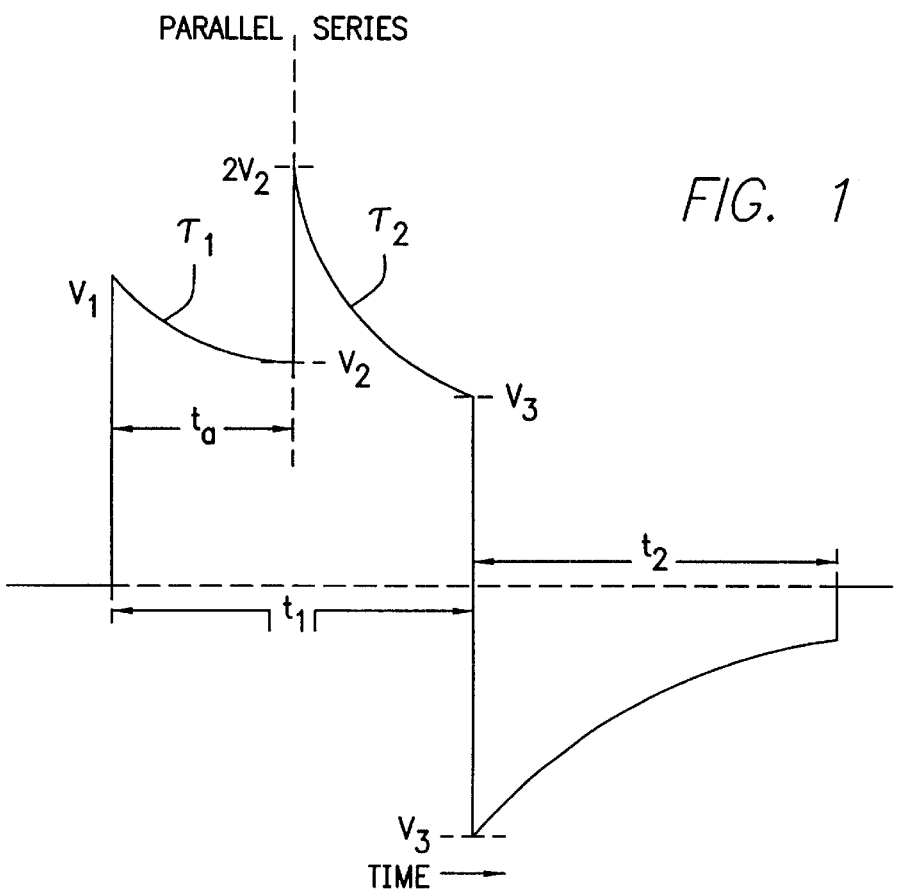
FIG. 1 illustrates a preferred defibrillation biphasic pulse or waveform generated in accordance with a two-capacitor ICD in accordance with the present invention.

In accordance with one aspect of the invention, then a biphasic pulse or waveform is generated by an ICD device having two capacitors that includes a positive phase of duration $t_1$ ms and a negative phase of duration $t_2$ ms, as shown in FIG. 1. First and second capacitors, $C_A$ and $C_B$, within the ICD device are initially charged to a voltage $V_1$ and are connected in parallel. The biphasic defibrillation pulse begins by discharging the charged parallel capacitors through the cardiac tissue by way of defibrillation electrodes in contact with the cardiac tissue. Thus, a leading edge of the biphasic pulse starts at a first peak voltage of approximately $V_1$ volts (the charge on the first and second capacitors when first connected to the electrodes).

During a first portion of the positive phase of the biphasic pulse, the amplitude of the biphasic pulse decays from the first peak voltage $V_1$ to a voltage $V_2$ in accordance with a first time constant $\tau_1$. The first time constant $\tau_1$ varies as a function of $(C_A+C_B)R$, where $C_A$ is the value of the first capacitor, $C_B$ is the value of the second capacitor, and R is an effective resistance associated with the discharge through the first and second electrodes.

A second portion of the positive phase begins by connecting the first and second capacitors in series. This sudden series connection increases the defibrillation pulse to a second peak voltage of approximately 2 ($V_2$) volts (the sum of the voltages on each of the first and second capacitors at the time the series connection is made), as illustrated in FIG. 1. The amplitude of the biphasic pulse decays during the second portion of the positive phase from the second peak voltage 2 ($V_2$) to a voltage $V_3$ in accordance with a second time constant $\tau_2$. The second time constant $\tau_2$ varies as a function of $(C_AC_B/C_AC_B))$ R. Advantageously, the voltage at the trailing edge of the positive phase, $V_3$, occurs at a time that is near the maximum cell membrane response.

The negative phase of the biphasic waveform begins by inverting the polarity of the series-connected first and second capacitors. Such negative phase thus commences at a third peak voltage of approximately $-V3$ volts, and decays thereafter towards zero in accordance with the second time constant $\tau_2$. After a prescribed time period $t_2$, the negative phase ends.

The biphasic waveform produced in accordance with the two-capacitor ICD is illustrated in FIG. 1. The first portion of the positive phase may terminate when either: (1) the voltage decreases below a threshold voltage $V_3$; or (2) a prescribed time period $t_a$ has elapsed.

Figure 2:
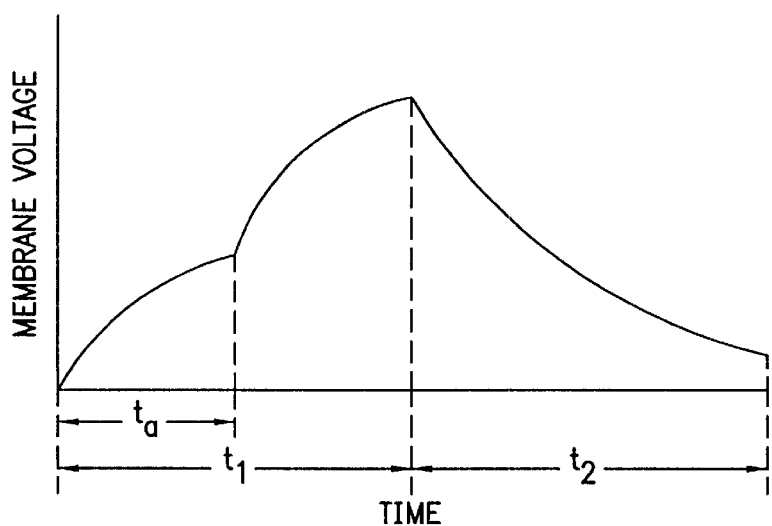
FIG. 2 depicts the excitable cardiac membrane response to the waveform of FIG. 1.

The tissue membrane voltage that results when the waveform of FIG. 1 is applied to excitable cardiac tissue membranes is as shown in FIG. 2. This membrane voltage is obtained by modeling the tissue membranes as taught in the Blair reference, previously cited. As shown in FIGS. 11–20, the optimum duration for $t_a$ will be described in more detail.

Figure 3:
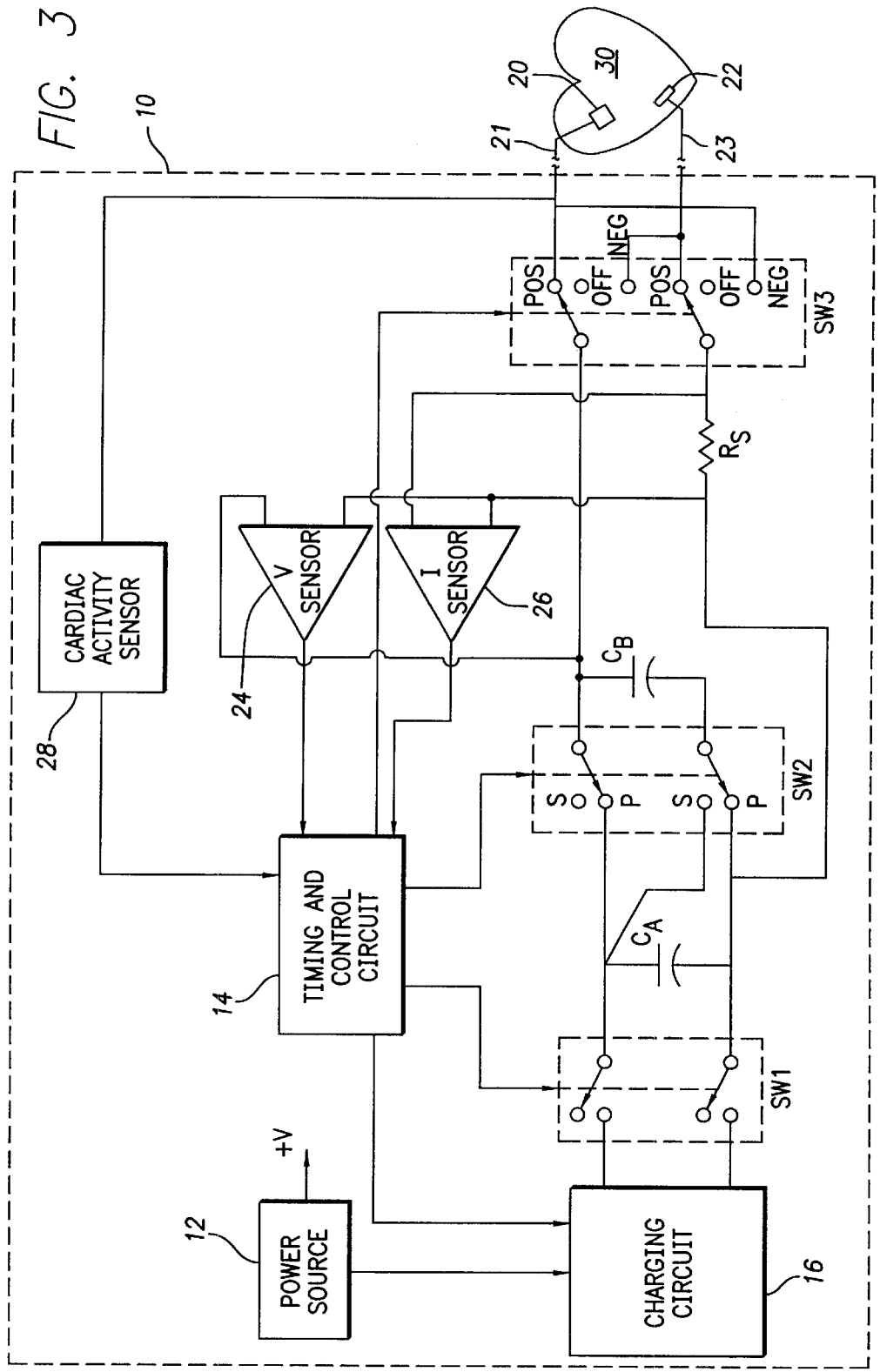
FIG. 3 is a functional block diagram of a two-capacitor ICD device, which generates the waveform of FIG. 1.

A functional block diagram of the pulse generation circuitry used to generate the biphasic waveform of the two-capacitor ICD is shown in FIG. 3.

As seen in FIG. 3, a cardiac tissue-stimulating device 10 includes a power source 12, e.g., at least one battery, a timing and control circuit 14, a charging circuit 16, an isolation switch network SW1, a series parallel switch network SW2, at least two capacitors $C_A$ and $C_B$, an output switch network SW3, and at least two electrodes 20 and 22.

The electrodes 20 and 22 are adapted to be positioned within or on the heart. The electrodes 20 and 22 are connected to the output switch SW3 through conventional leads 21 and 23, respectively.

A voltage sense amplifier 24 senses the voltage held on the capacitor $C_B$ (which will be the same voltage as capacitor $C_A$ when $C_A$ and $C_B$ are connected in parallel). In some embodiments of the invention, a current sense amplifier 26 may also be used to sense the current flowing to or returning from one of the electrodes 20 or 22. In FIG. 3, such current is sensed by differentially measuring the voltage across a small current-sense resistor $R_S$ connected in series with electrode 22. The outputs of the voltage sense amplifier 24 and the current sense amplifier 26 are directed to the timing and control circuit 14.

A suitable cardiac activity sensor 28 is also employed within the device 10 in order to detect cardiac activity. The function of the sensor 28 is to sense cardiac activity so that an assessment can be made by the timing and control circuitry whether a defibrillation pulse needs to be generated and delivered to the cardiac tissue. Such sensor 28 may take many forms, e.g, a simple R-wave sense amplifier of the type commonly employed in implantable pacemakers. The details of the sensor 28 are not important for purposes of the present invention.

The power source 12 is connected to provide operating power to all components and circuitry within the device 10. The power source 12 also provides the energy needed to generate the biphasic defibrillation pulse. That is, energy stored within the power source 12 is used to charge capacitors $C_A$ and $C_B$, through the charging circuit 18, up to the desired initial defibrillation starting pulse voltage $V_1$. Such charging is carried out under control of the timing and control circuit 14. Typically, $V_1$ may be a relatively high voltage, e.g., 350 volts, even though the power source 12 may only be able to provide a relatively low voltage, e.g., 3–6 volts. The charging circuit 16 takes the relatively low voltage from the power source 12 and steps it up to the desired high voltage $V_1$, using conventional voltage step-up techniques as are known in the art. This stepped-up voltage $V_1$ is then applied through the isolation switch SW1 to both capacitors $C_A$ and $C_B$ at a time when $C_A$ and $C_B$ are connected in parallel, i.e., when SW2 is in its "P" position, and at a time when the output switch is in its open, or OFF, position. As the capacitors $C_A$ and $C_B$ are being charged, the voltage sense amplifier 24 monitors the voltage level on the capacitors. When the desired voltage $V_1$ has been reached, the timing and control circuitry 14 turns off the charging circuit 16 and opens the isolation switch SW1, thereby holding the voltage $V_1$ on capacitors $C_A$ and $C_B$ until such time as a defibrillation pulse is needed.

When a defibrillation pulse is called for by the timing and control circuit 14, the output switch SW3 is placed in its positive phase position, POS, thereby connecting the parallel connected capacitors $C_A$ and $C_B$ (on which the starting voltage $V_1$ resides) to the cardiac tissue through the electrodes 20 and 22. Such connection starts the discharge of capacitors $C_A$ and $C_B$ through the cardiac tissue in accordance with the first time constant $\tau_1$ as described above in connection in FIG. 1.

After a period of time $t_a$, or as soon as the voltage across the parallel-connected capacitors $C_A$ and $C_B$ has decreased to the threshold value $V_2$ (as sensed by the voltage sense amplifier 24), the timing and control circuit switches SW2 to its series-connected or "S" position, thereby connecting the capacitors $C_A$ and $C_B$ in series across the electrodes 20 and 22. Such series connection doubles the voltage across the electrodes 20 and 22 to a value of 2($V_2$) Thereafter, the discharge of the series-connected capacitors $C_A$ and $C_B$ continues through the cardiac tissue in accordance with the second time constant $\tau_2$ as described above. This discharge continues until the end of the positive phase.

The positive or first phase ends at a time $t_1$ from the beginning of the positive phase (as measured by timing circuits within the timing and control circuit 14), or when the voltage has decayed to a value $V_3$ (as sensed by voltage sense amplifier 24). Alternatively, the positive phase may end as a function of the sensed current (as sensed by the current sense amplifier 26), e.g., at a time when the sensed current has decreased from a peak value by a prescribed amount or percentage.

As soon as the positive phase ends, the timing and control circuit 14 switches the output switch SW3 to the negative phase position, NEG, thereby reversing the polarity of the discharge of the series-connected capacitors $C_A$ and $C_B$ through the cardiac tissue. The negative phase lasts thereafter for a time period $t_2$ determined by the timing and control circuitry.

The functions represented by the functional block diagram of FIG. 3 may be implemented by those of skill in the art using a wide variety of circuit elements and components. It is not intended that the present invention be directed to a specific circuit, device or method; but rather that any circuit, device or method which implements the functions described above in connection with FIG. 3 to produce a defibrillation waveform of the general type shown in FIG. 1 be covered by the invention.

Turning next to FIG. 4, there is shown a simplified schematic diagram of an ICD having three 120 $\mu$F capacitors C1, C2 and C3. The manner of charging the capacitors while they are connected in parallel is the same or similar to that shown in FIG. 3. When the capacitors C1, C2 and C3 have been charged to a high voltage, e.g., 370 V, a stored energy of approximately 25 Joules is realized. Once the capacitors have been charged by the ICD, the capacitors are configured for a parallel discharge. This is accomplished by closing switches S1, S2, S3 and S4, while maintaining switches S5 and S6 open. The parallel discharge takes place from time t=0 until a time $d_1$. Once $d_1$ elapses, one of two options may be used to discharge the remaining charge.

In accordance with a first option, or Option 1, after $d_1$ has elapsed (i.e., after the capacitors are discharged in parallel until time $d_1$), all of the capacitors are discharged in series for the remainder of the pulse. This is accomplished by opening S1, S2, S3 and S4 and closing S5 and S6. At a later time, $d_2$, the "H Bridge" circuit 40 (FIG. 4) is used to reverse the polarity of the output. At yet a later time, d, the output pulse is truncated.

The waveform generated in accordance with Option 1 is illustrated in FIG. 5. The tissue membrane voltage associated with the waveform of FIG. 5 is modeled and computed, using the Blair model, as shown in FIG. 6. For the example shown in FIGS. 5 and 6, the optimum value of $d_1$ is nominally about 3.5 ms. The optimum choice of $d_2$ is when the elapsed time at $d_2$ is about 1.5 times the elapsed time at $d_1$, or when the elapsed time at $d_2$ (from t=0) is about 5.25 ms.

Figure 7:
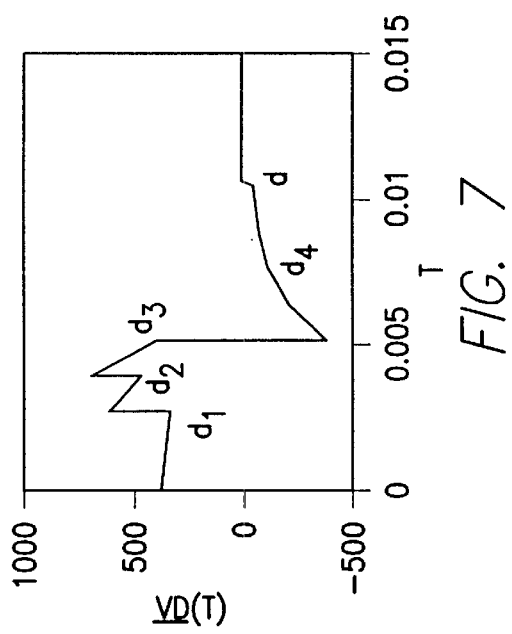
FIG. 7 illustrates another type of defibrillation waveform that may be generated using the ICD of FIG. 4.

In accordance with a second option, or Option 2, the capacitors C1 and C2 remain in parallel and are in series with C3 until time $d_2$. This is accomplished by opening S3 and S4 and closing S6. After $d_2$ all the capacitors are in series (S1 and S2 also open, S5 closed) until C3 runs out of charge at a time $d_4$. After $d_4$, the diode $D_1$ bypasses the depleted capacitor and the time constant of discharge is of C1 and C2 in series. At a time $d_3$, where $d_2 < d_3 < d_4$, the polarity of the output is reversed using the H Bridge 40. The pulse is truncated at time d. The resulting waveform is shown in FIG. 7. The resulting membrane voltage is modeled and computed and shown in FIG. 8.

Figure 8:
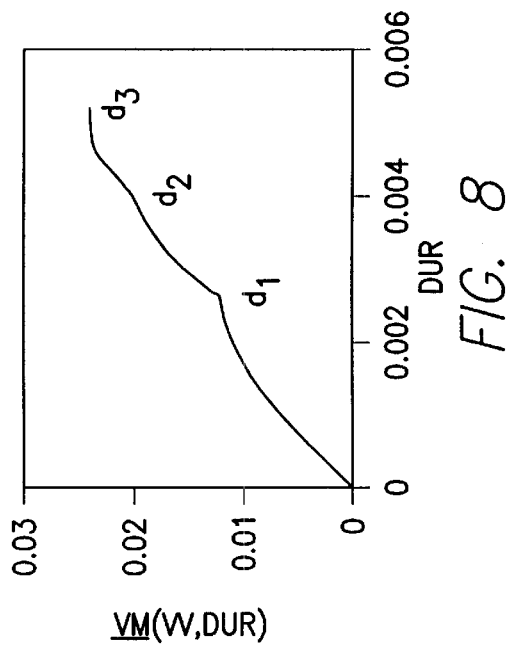
FIG. 8 depicts the excitable cardiac membrane response during phase 1 (positive phase) to the waveform of FIG. 7.

For the example shown in FIGS. 7 and 8, the optimum values of $d_1$ is 2.7 ms, $d_2$ is 1.5 times $d_1$ (or about 4 ms), $d_3$ is $d_2$+1.25 ms. The value of $d_4$ is computed to be about 7.6 ms. The choice of d can be in the range of 1.5 to 2.0 times that of $d_3$.

With either Option 1 or Option 2, the choice of the values $d_1$, $d_2$ and $d_3$ are primarily functions of the ICD's capacitance value, the discharge pathway impedance, and the tissue time constant ($\tau_m$).

The advantage of Option 2 is that the peak waveform voltage is lower than Option 1 yet a minute increase in membrane voltage over Option 1 is achieved. However, Option 1 is simpler to implement and diode $D_1$ is not needed since all the capacitors are discharged equally.

Figure 10:
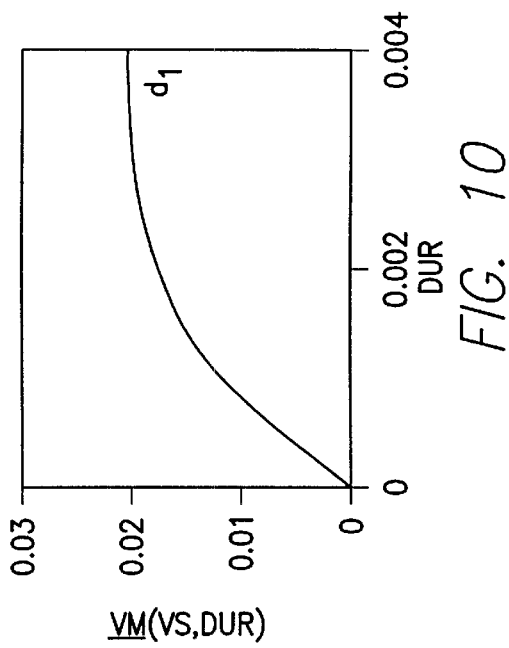
FIG. 10 illustrates, again for comparative purposes, the membrane response during phase 1 (positive phase) to the waveform of FIG. 9.
Figure 9:
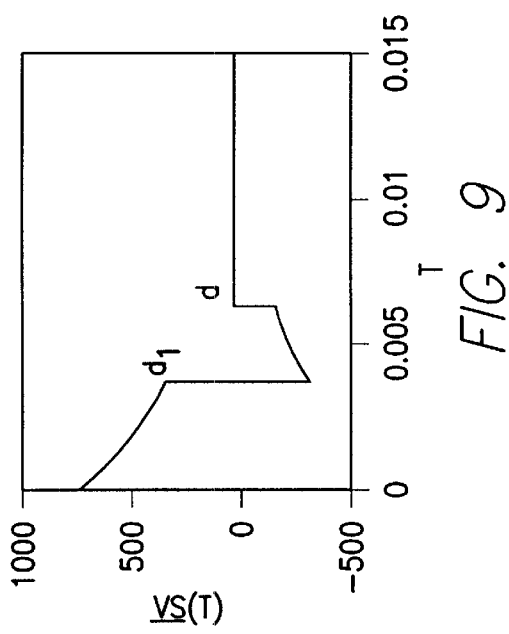
FIG. 9 illustrates, for comparative purposes, the biphasic defibrillation waveform typically provided by a two-capacitor ICD of the prior art.

The advantages of either Option 1 or Option 2 are better appreciated by comparing the results of such discharge, as presented in FIGS. 5, 6, 7 and 8, with the corresponding discharge achieved with a two-capacitor ICD series discharge, as is commonly used in a conventional ICD of the prior art. The discharge waveform achieved with a conventional two-capacitor ICD using series discharge, and the resulting membrane voltage, is shown in FIGS. 9 and 10, respectively. Note, that to store equal energy to the three capacitor ICD, each capacitor of the two-capacitor ICD must have 1.5 times the capacitance value, or two capacitors each with C=180 $\mu$F.

As can be seen from a comparison of FIGS. 9 and 10 with FIGS. 5 and 6 (Option 1), and 5A and 5B (Option 2), for equal stored energy, the value of the peak membrane voltage for Option 2 is 1.18 times higher than the membrane voltage realized using the conventional waveform. Similarly, Option 1 yields a membrane voltage that is 1.17 times higher than is realized using the conventional waveform. In other words, a 25 Joule ICD with three 120$\mu$F capacitors and a switching network as in Option 2 performs equally to a 34.4 Joule conventional ICD with two 180$\mu$F capacitors. This represents a remarkable improvement in performance.

Figure 11:
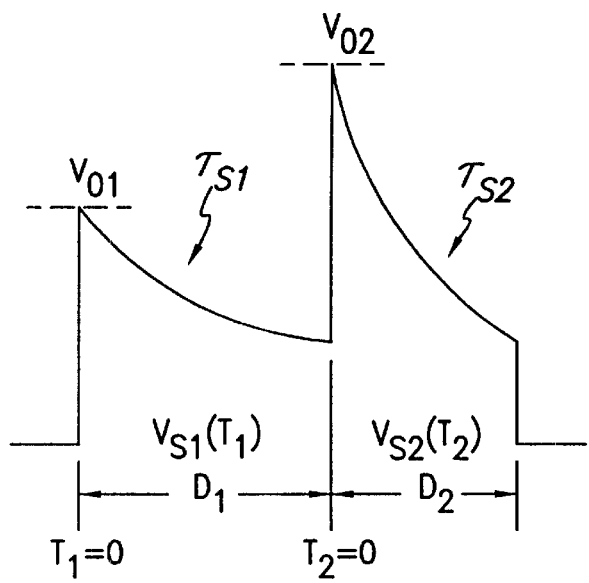
FIG. 11 shows the first phase of a parallel/series discharge waveform with the durations and time constants defined.

As shown in FIG. 11, the two-step waveform has been reproduced. Although identical in nature to that shown in FIG. 1, the designators have been changed slightly for purposes of the in depth analysis that will follow.

As described above in conjunction with FIG. 3, two capacitors, $C_A$ & $C_B$, have been charged to the same initial voltage, $V_{01}$. The system resistance (as seen by device) is given by $R_S$. For purposes of this discussion, the myocardium has been modeled as a parallel-RC circuit with myocardial tissue time constant, $\tau_m$.

The amplitude of each step of the positive portion of the defibrillation waveform, shown in FIG. 11, can be characterized with the following basic equations:

$$V_{s1}(t_1) = V_{01} \cdot \exp[-t_1/\tau_{s1}] \quad 0 \leq t_1 \leq d_1$$

$$V_{s2}(t_2) = V_{02} \cdot \exp[-t_2/\tau_{s2}] \quad 0 \leq t_2 \leq d_2$$

wherein:
  $V_{S1}$ is the exponential decay during the first period, $t_1$, (i.e., Step1);
  $V_{S2}$ is the exponential decay during the second period, $t_2$, (i.e., Step2);

$\tau_{S1}$ is the time constant of $C_A$ and $C_B$ in parallel;

$\tau_{S2}$ is the time constant of $C_A$ and $C_B$ in series;

$V_{O1}$ is the initial voltage during Step1 on the capacitors $C_A$ and $C_B$ once fully charged to the source voltage, $V_{O1}$; and $V_{O2}$ is the initial voltage during Step2 remaining on the capacitors $C_A$ and $C_B$ now configured in series.

The analysis that follows directly will explain how to determine the absolute and approximate solutions for the optimal durations, $d_1$ and $d_2$, to maximize induced myocardial potential, $V_m(t)$, when the two capacitors are arranged in a parallel-series, two-step arrangement.

Consider the myocardial responses to $V_{s1}(t_1)$ [Step1] and $V_{s2}(t_2)$ [Step2] separately. Note that the following derivations (Equations 1–4) make absolutely no assumptions regarding any specific relationships between the characteristics of Step1 and Step2.

The "Step1" myocardial response, $V_{m1}$, to the Step1 waveform, $V_{s1}$, is described by:

$$\frac{dV_{m1}(t_1)}{dt_1} + \frac{V_{m1}(t_1)}{\tau_m} \propto \frac{V_{s1}(t_1)}{\tau_m} \quad \text{(Eq. 1)}$$

with the initial condition: $V_{m1}(0)=0$.

The solution to this differential equation is:

$$V_{m1}(t_1) = \begin{cases} \frac{V_{O1}}{\alpha_1} \cdot \left(\exp\left[\frac{-t_1}{\tau_{s1}}\right] - \exp\left[\frac{-t_1}{\tau_m}\right]\right) & \tau_{s1} \neq \tau_m \\ \frac{V_{O1}}{\tau_{s1}} \cdot \left(t_1 \cdot \exp\left[\frac{-t_1}{\tau_{s1}}\right]\right) & \tau_{s1} = \tau_m \end{cases} \quad \text{(Eq. 2)}$$

where $\alpha_1 = 1 - (\tau_m/\tau_{s1})$.

The "Step2" myocardial response, $V_{m2}$, to the Step2 waveform, $V_{s2}$, is governed by:

$$\frac{dV_{m2}(d_1, t_2)}{dt_2} + \frac{V_{m2}(d_1, t_2)}{\tau_m} \propto \frac{V_{s2}(t_2)}{\tau_m} \quad \text{(Eq. 3)}$$

with the initial condition: $V_{m2}(d_1,0)=V_{m1}(d_1)$, where $d_1$ represents the final duration of Step1.

This initial condition ensures that there is a continuity of myocardial voltage when transitioning from the end of Step1 into the start of Step2. The solution to this differential equation is:

$$V_{m2}(d_1, t_2) = V_{m1}(d_1) \cdot \exp\left[\frac{-t_2}{\tau_m}\right] + \quad \text{(Eq. 4)}$$

$$\begin{cases} \frac{V_{O2}(d_1)}{\alpha_2} \cdot \left(\exp\left[\frac{-t_2}{\tau_{s2}}\right] - \exp\left[\frac{-t_2}{\tau_m}\right]\right) & \tau_{s2} \neq \tau_m \\ \frac{V_{O2}(d_1)}{\tau_{s2}} \cdot \left(t_1 \cdot \exp\left[\frac{-t_2}{\tau_{s2}}\right]\right) & \tau_{s2} = \tau_m \end{cases}$$

where $\alpha_2 = 1-(\tau_m/\tau_{s2})$, and $V_{O2}$ is proportional to $V_{s2}(0)$ Equation (4) describes a curve with a single maximum value. The step durations, $d_1=d_1^{opt}$ and $d_2=d_2^{opt}$, that maximize this shock-induced myocardial voltage, $V_{m2}(t_1, t_2)$ can be determined by solving the simultaneous equations given by:

$$\frac{\partial V_{m2}(d_1^{opt}, d_2^{opt})}{\partial d_1^{opt}} = 0 \quad \frac{\partial V_{m2}(d_1^{opt}, d_2^{opt})}{\partial d_2^{opt}} = 0 \quad \text{(Eq. 5)}$$

From Equation (5), two equations that describe $d_2^{opt}$ as a function of $d_1^{opt}$ can be found (the following derivations assume $\tau_{s1} \tau_m$ and $\tau_{s2} \tau_m$):

$$d_2^{opt} = \frac{\tau_m}{\alpha_2} \cdot \ln\left\{1 + \left(\frac{\alpha_2}{\alpha_1} \cdot \frac{V_{O1}}{\partial V_{O2}/\partial d_1^{opt}}\right) \cdot \right. \quad \text{(Eq. 6)}$$

$$\left. \left(\frac{1}{\tau_{s1}}\exp\left[\frac{-d_1^{opt}}{\tau_{s1}}\right] - \frac{1}{\tau_m}\exp\left[\frac{-d_1^{opt}}{\tau_m}\right]\right)\right\}$$

$$d_2^{opt} = \quad \text{(Eq. 7)}$$

$$\frac{\tau_m}{\alpha_2} \cdot \ln\left\{\frac{\tau_{s2}}{\tau_m}\left[1 - \left(\frac{\alpha_2}{\alpha_1} \cdot \frac{V_{O1}}{V_{O2}(d_1^{opt})}\right) \cdot \left(\exp\left[\frac{-d_1^{opt}}{\tau_{s1}}\right] - \exp\left[\frac{-d_1^{opt}}{\tau_m}\right]\right)\right]\right\}$$

Setting Equations (6) and (7) equal to each other and simplifying produces the following implicit equation for $d_1^{opt}$:

$$\left(\frac{\tau_m}{\tau_{s2}} \cdot \frac{\alpha_1}{V_{O1}}\right) = \left(\frac{1/\tau_{s1}}{\partial V_{O2}/\partial d_1^{opt}} + \frac{\tau_{s2}/\tau_m}{V_{O2}(d_1^{opt})}\right)\exp\left[\frac{-d_1^{opt}}{\tau_{s1}}\right] - \quad \text{(Eq. 8)}$$

$$\left(\frac{1/\tau_m}{\partial V_{O2}/\partial d_1^{opt}} + \frac{\tau_{s2}/\tau_m}{V_{O2}(d_1^{opt})}\right)\exp\left[\frac{-d_1^{opt}}{\tau_m}\right]$$

Further simplifications of Equation (8) require that $V_{O2}(d_1)$ be explicitly defined.

When the two system capacitors ($C_A$ & $C_B$) are configured into a parallel arrangement during Step1 and then reconfigured into a series arrangement during Step2, the system time constants can be explicitly defined as:

$$\tau_{s1}=R_S \cdot (C_A+C_B) \quad \tau_{s2}=R_S \cdot (C_A C_B)/(C_A+C_B) \quad \text{(Eq. 9)}$$

Furthermore, $V_{O2}(d_1)$ is explicitly defined as:

$$V_{O2}(d_1)=2 \cdot V_{s1}(d_1) = 2 \cdot V_{O1} \cdot \exp[-d_1/\tau_{s1}] \quad \text{(Eq. 10)}$$

where Equation (10) codifies the notion that, in a parallel-series arrangement, the leading edge voltage of Step2 equals twice the trailing edge voltage of Step1.

Substituting Equation (10) into Equation (8) and solving explicitly for $d_1^{opt}$ and subsequently $d_2^{opt}$ [via Equation (6) or (7)] yields:

$$d_1^{opt} = -\frac{\tau_m}{\alpha_1} \cdot \ln\left\{\left(\frac{\tau_m}{\tau_{s1}}\right)\left(\frac{2\alpha_1 - \alpha_2}{\alpha_1 - \alpha_2}\right)\right\} \quad \text{(Eq. 11)}$$

$$d_2^{opt} = +\frac{\tau_m}{\alpha_1} \cdot \ln\left\{\left(\frac{1}{2}\right)\left(\frac{2\alpha_1 - \alpha_2}{\alpha_1 - \alpha_2}\right)\right\} \quad \text{(Eq. 12)}$$

The maximum myocardial voltage attained using these optimal parallel-series step durations can then be determined by substituting Equations (10)–(12) into Equation (4) and simplifying:

$$V_{m2}(d_1^{opt}, d_2^{opt}) = V_{01}\left(\frac{1}{2}\right)^{-\frac{1}{\alpha_2}} \left(\frac{\tau_m}{\tau_{s1}}\right)^{\frac{1}{\alpha_1}-1} \left(\frac{2\alpha_1 - \alpha_2}{\alpha_1 - \alpha_2}\right)^{\frac{1}{\alpha_1} - \frac{1}{\alpha_2}} \quad \text{(Eq. 13)}$$

Note that Equations (11)–(13) are valid for any independent values of $C_A$ and $C_B$.

According to this simple RC model of defibrillation, successful defibrillation is achieved when the myocardial voltage (as embodied herein by $V_{m1}$ and $V_{m2}$) is "depolarized" to its threshold value, $V_{th}$. An equation that describes the minimum relative magnitude for $V_0$ (i.e., the voltage to which each of the capacitors is charged in preparation for the defibrillation shock) that successfully drives $V_{m2}$ to $V_{th}$ can be obtained from Equation (13) by setting $V_{m2}=V_{th}$ and solving for $V_{01}$ (which, for these parallel-series shocks, is equivalent to $V_0$).

Since the total stored energy in capacitors $C_A$ and $C_B$ is given by:

$$E_{stored} = \frac{1}{2}(C_A + C_B) \cdot V_0^2 \quad \text{(Eq. 14)}$$

then the optimal relationship between $C_A$ and $C_B$ that maximizes myocardial voltage for a given total stored energy can be found by substituting $C_A = k \cdot C_B$ into Equation (14) and then solving for k in $\partial E_{stored}/\partial k = 0$. The result is:

$$k^{opt} = C_A/C_B = 1 \quad \text{(Eq. 15)}$$

The above result implies that $C_A$ should equal $C_B$ in order to achieve maximum myocardial impact for any given total energy. The relationship $C_A = C_B$ is equivalent to $\tau_{s1} = 4\tau_{s2}$ [see Equation (9)], from which simplified versions of Equations (11)–(13) can be derived:

$$d_1^{opt} = -\frac{\tau_m}{\alpha_1} \cdot \ln\left\{\left(\frac{1}{3}\right)\left(1 + \frac{\tau_m}{2\tau_{s2}}\right)\right\} \quad \text{(Eq. 16)}$$

$$d_2^{opt} = +\frac{\tau_m}{\alpha_2} \cdot \ln\left\{\left(\frac{1}{3}\right)\left(1 + \frac{2\tau_{s2}}{\tau_m}\right)\right\} \quad \text{(Eq. 17)}$$

$$V_{m2}(d_1^{opt}, d_2^{opt}) = 2\left(V_{01}\left(\frac{\tau_m}{2\tau_{s2}}\right)\right)^{\frac{1}{\alpha_2}-1}\left[\left(\frac{1}{3}\right)\left(1 + \frac{\tau_m}{2\tau_{s2}}\right)\right]^{\frac{1}{\alpha_1}-\frac{1}{\alpha_2}} \quad \text{(Eq. 18)}$$

Finally, the optimal capacitance for a given $R_s$ and $\tau_m$ is determined by finding the value of $C_A$ that minimizes $E_{stored}$, that is, solving for $C_A$ in $\partial E_{stored}/\partial C_A = 0$ (with k=1). The result is:

$$C_A = C_B = \frac{\tau_m}{R_s} \quad \text{(Eq. 19)}$$

or equivalently, the optimal capacitance (for a given $R_s$ and $\tau_m$) is that which satisfies:

$$\frac{1}{2}\tau_{s1} = 2\tau_{s2} = \tau_m \quad \text{(Eq. 20)}$$

Under these ideal conditions, the optimal step durations are:

$$d_1^{opt} = +2\tau_m \cdot \ln[3/2] \approx 0.811 \cdot \tau_m \quad \text{(Eq. 21)}$$

$$d_2^{opt} = +\tau_m \cdot \ln[3/2] \approx 0.405 \cdot \tau_m \quad \text{(Eq. 22)}$$

Figure 12:
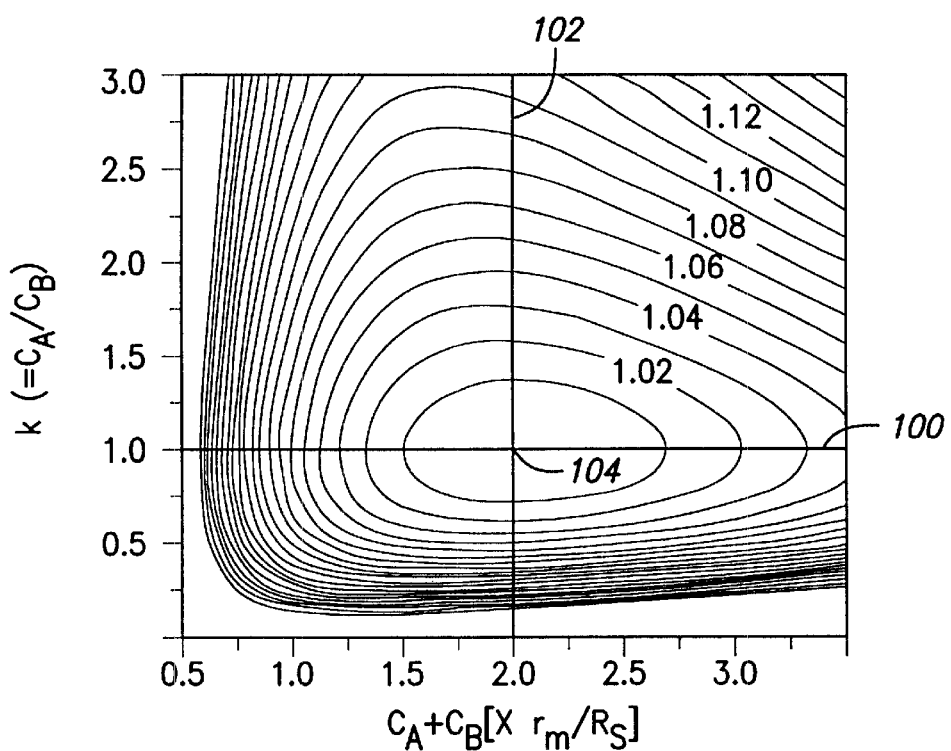
FIG. 12 shows a first contour plot of stored energy as a function of a scaling factor "K" (equivalent to $C_A/C_B$ and the total capacitance ($C_A/C_B$ as scaled by $\tau_m/R_S$)

Further insights into the preceding theoretical calculations can be gleaned from corresponding graphical analyses. The relative stored energy required for defibrillation ($E_{stored}$) for all possible parallel-series two-step waveforms is graphically illustrated in the contour plot of FIG. 12. In this plot, the x-axis is indexed by the total capacitance ($C_A + C_B$, scaled by $\tau_m/R_s$) while the y-axis is indexed by the ratio of the two capacitances ($k = C_A/C_B$). Although perhaps seemingly non-intuitive axis definitions, they efficiently provide complete coverage of the entire parameter space of all possible capacitor combinations for two-step waveforms. As indicated by the horizontal line 100 and the vertical line 102 overlaid on this plot (and as consistent with the conclusions of Equations (15) and (19)), the most efficient two-step positive portion for the biphasic shock is delivered when:

k=1.0; and $C_A + C_B = 2 \cdot \tau_m/R_s$;

which occurs at point 104 in FIG. 12.

The contours then step out from this optimal point in 1% increments, thus providing an indication as to the relative sensitivity of the energy efficiency to deviations in either total capacitance or capacitance ratio. In fact, energy efficiency remains quite robust: for example, energy efficiency remains within 1% of optimal for:

~1.5·$\tau_m/R_s$ < ($C_A + C_B$) < ~2.7·$\tau_m/R_s$; and 0.7 < k < 1.4.

Figure 13:
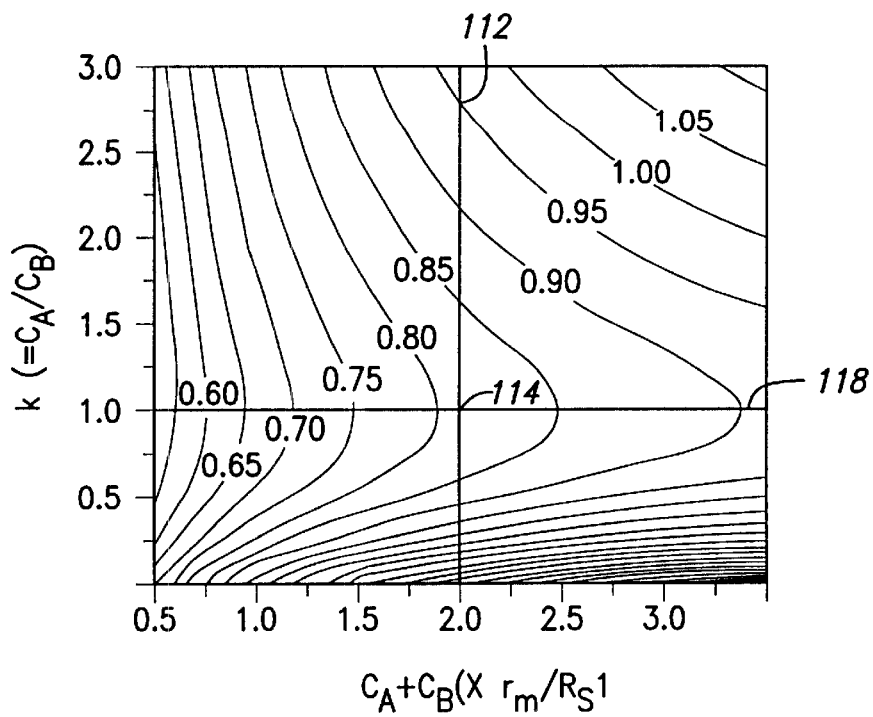
FIGS. 13 and 14 show a second and third contour plot of the $d_1$ and $d_2$, respectively, as a function of the scaling factor K and the total capacitance, wherein the optimal value occurs at the cross-hair.
Figure 14:
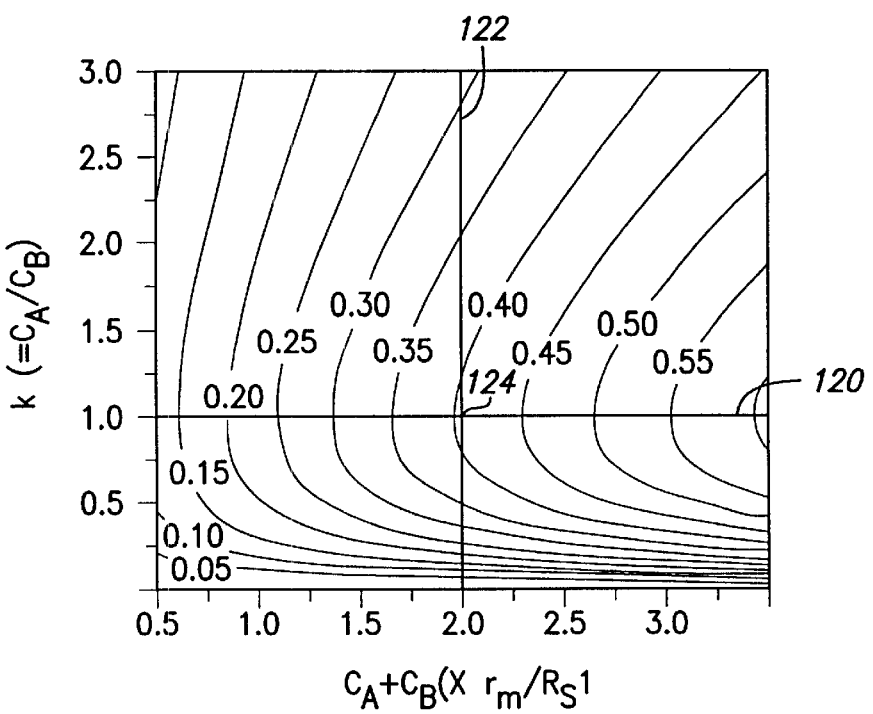

Two-dimensional contour plots of optimal Step1 and Step2 durations (normalized by $\tau_m$, i.e., $d_1^{opt}/\tau_m$ and $d_2^{opt}/\tau_m$) as given by Equations (11) and (12) are presented in FIGS. 13 and 14, respectively.

Similar to FIG. 12, FIGS. 13 and 14 have respective horizontal lines 110, 120 and vertical lines 112, 122 from have been overlaid on these contour maps as well. Their respective intersections 114, 124 appropriately correspond to the "0.811" and "0.405" coefficients found in Equations (21) and (22), respectively.

Since $R_S$ and $\tau_m$ represent patient-specific variables that directly impact the choice of durations used for these stepped waveforms, it is perhaps useful to present example values for $d_1^{opt}$ and $d_2^{opt}$ for a representative range of values for $R_s$ (30–90 Ω), $\tau_m$ (2–4 ms), and $C_A$ (30–90 μF). The tables shown in FIGS. 15–17 provide such a set of example values, wherein values for $d_1^{opt}$ and $d_2^{opt}$ are computed from Equations (16) and (17), respectively.

Given the limits of the ranges used for $R_s$, $\tau_m$, and $C_A$ in the tables shown in FIGS. 15–17, $d_1^{opt}$ and $d_2^{opt}$ range from lows of 1.286 and 0.422 ms (when $\tau_m = 2$ ms, $C_A = 30$ μF, and $R_s = 30$ Ω) to highs of 3.704 and 2.689 ms (when $\tau_m = 4$ ms, $C_A = 90$ μF, and $R_s = 90$ Ω), respectively.

To summarize the above, for the ranges of:

$\tau_m = 2$–4 ms;

$R_s = 30$–90 Ω;

$C_A = C_B = 30$–90 μF

Then, the optimum durations fall in the ranges:

$d_1^{opt} = 1.286$–3.704

$d_2^{opt} = 0.422$–2.689

Of course, $d_1^{opt}$ and/or $d_2^{opt}$ could move outside of these ranges if any one or more of $R_s$, $\tau_m$, and $C_A$ exceed the limits used for these tables. In those cases, Equations (16) and (17)

could be used to compute exactly the optimal step durations for any combination of $R_s$, $\tau_m$, and $C_A$.

In another embodiment, the device could also determine $d_1^{opt}$ and $d_2^{opt}$ based on measured values for $R_s$, and/or a programmed value for $\tau_m$, based on a particular value for $C_A$ and $C_B$.

Figure 18:
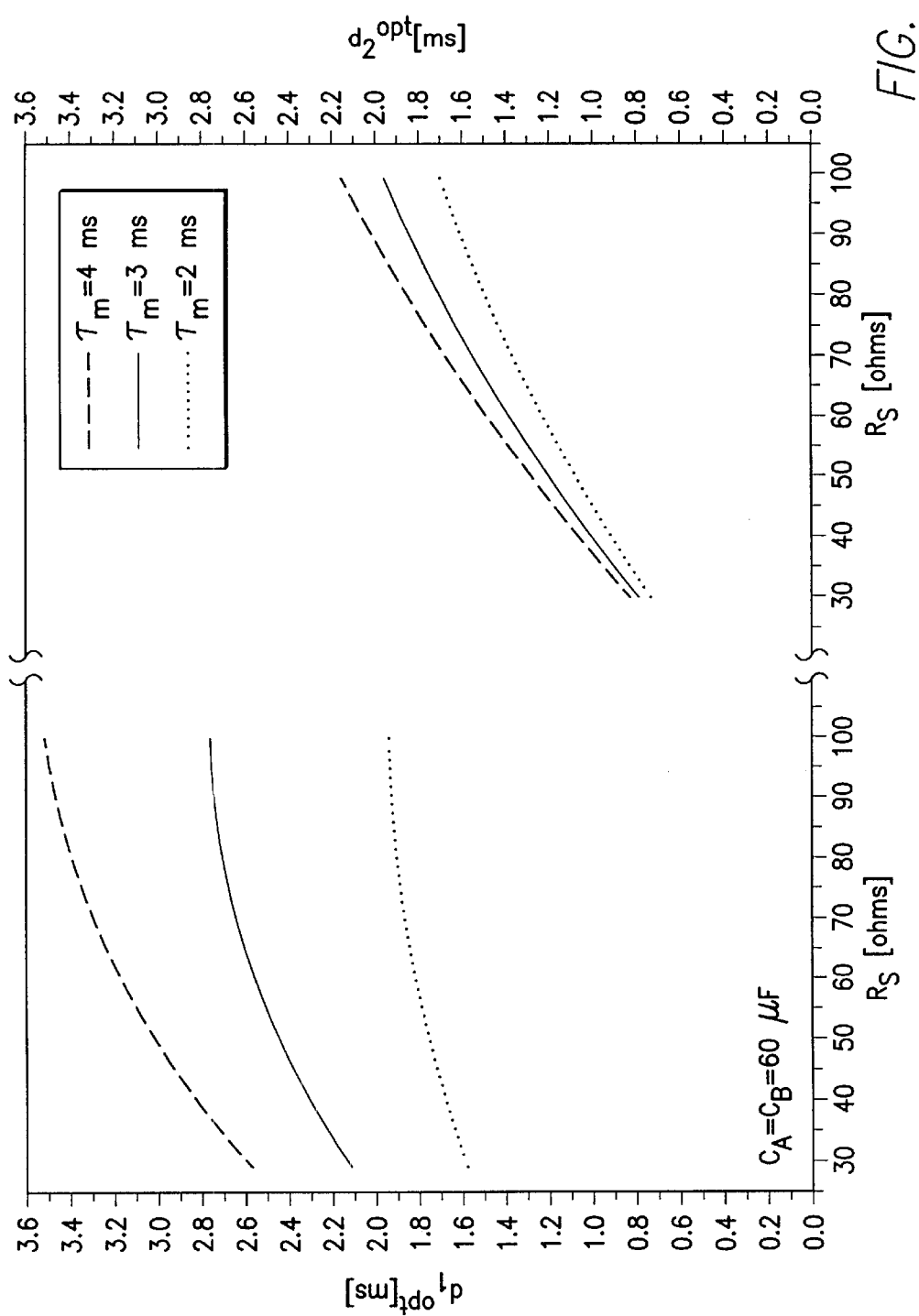
FIG. 18 is a graph of optimal durations for $d_1$ and $d_2$ as a function of tissue resistance ($R_S$) for desired (e.g., 60 $\mu F$) capacitor and a range of tissue time constants ($\tau_m$)

By way of example, if the capacitance value for $C_A$ and $C_B$ is set to 60 μF, so that Equation 19 is satisfied for a tissue resistance, $R_s$ equal to nominally 50 ohms and a tissue time constant, $\tau_m$, then for a range for $\tau_m$ of 2 ms to 4 ms, and a range for $R_s$ of 30–90 ohms, then:

If $\tau_m$=2.0 ms and Rs=90 ohms, then:

$(C_A+C_B)*R_s/\tau_m=5.4$ $d_1^{opt}=0.962 * \tau_m(=1.923\text{ ms})$ $d_2^{opt}=0.809 * \tau_m(=1.618\text{ ms})$ If $\tau_m$=4.0 ms and Rs=30 ohms, then:

$(C_A+C_B)*R_s/\tau_m=0.9$ $d_1^{opt}=0.643 * \tau_m (=2.573\text{ ms})$ $d_2^{opt}=0.211 * \tau_m (=0.844\text{ ms})$ To further assist with interpreting the results embodied in FIGS. 13 and 14 and the table shown in FIGS. 15–17, FIG. 18 graphs a subset of those data as simple functions of $R_s$ and $\tau_m$. In particular, FIG. 18 presents a pair of graphs: the left and right halves plot $d_1^{opt}$ and $d_2^{opt}$, respectively, as functions of $R_s$ for three representative values of $\tau_m$ (2, 3, and 4 ms). For these graphs, $C_A=C_B=60$ μF (thus k=1.0). Consistent with the data in the tables shown in FIGS. 15–17 both $d_1^{opt}$ and $d_2^{opt}$ increase in value with increasing $R_s$ or $\tau_m$. Moreover, this figure helps illustrate how $d_1^{opt}$ appears significantly more sensitive to relative changes in $\tau_m$ than in $R_s$, while $d_2^{opt}$ appears to have the opposite sensitivity.

While FIGS. 12–17 provide a comprehensive overview of all possible parallel-series two-step waveforms, it is also useful to consider some specific examples that can aid in illustrating the relative improvements gained by using such a parallel-series two-step capacitor arrangement over the traditional one-step arrangement.

Figure 19:
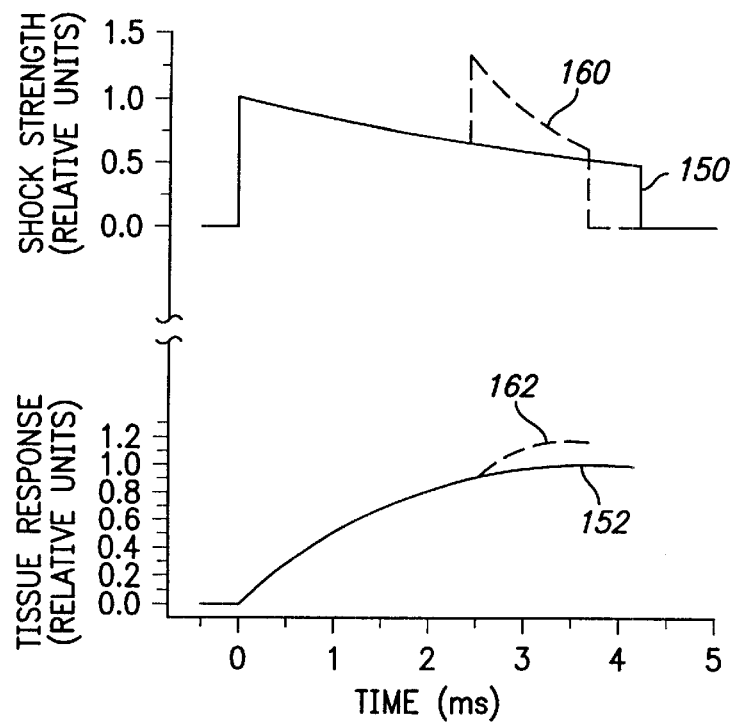
FIG. 19 illustrates a single-step and a two-step (parallel/series) waveform of equal stored energy and their resulting cell membrane responses.

FIG. 19 graphically compares the positive portion of the biphasic shock waveform shapes ($V_s$, top two waveforms, 150 and 160) and associated tissue responses ($V_m$, bottom two waveforms, 152 and 162) for one-step, 150, and parallel-series two-step, 160, shocks having equal stored energies and leading-edge voltages.

For this example, shown in FIG. 19:

$\tau_m$=3 ms, $R_s$=50 Ω, $C_A=C_B$=60 μF (thus, Equations 15 & 19 are satisfied).

The one-step shock is generated by essentially keeping $C_A$ and $C_B$ in a parallel arrangement for its entire shock duration, for a constant effective capacitance of 120 μF. As is evident from the tissue responses (i.e., comparing the one-step response 152 to the two-step response 162), two-step the myocardial voltage (162) reaches a higher higher final cell membrane potential (+18.6%) in a shorter total duration (3.65 vs. 4.16 ms ⇒12.3%) as compared to the final cell membrane potential (152) using the one-step shock. A consequence of this improved tissue response is that this two-step waveform requires a lower effective leading-edge voltage (and hence a lower stored energy) to achieve the same defibrillation efficacy as its equivalent one-step waveform.

Figure 20:
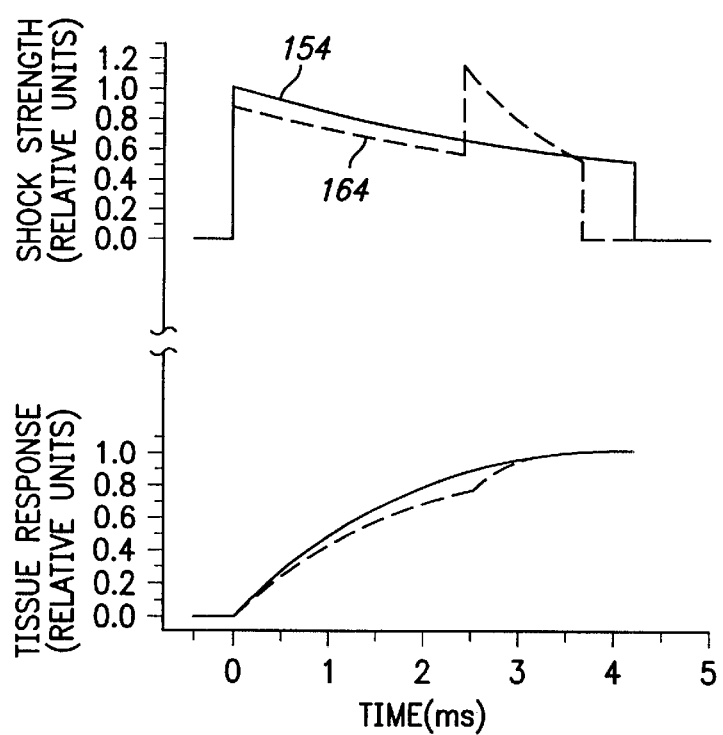
FIG. 20 illustrates the single-step and the two-step waveforms normalized to achieve the maximum cell member response.

FIG. 20 illustrates this scenario by resealing the results presented in FIG. 19 such that the strength of each shock is sufficient to produce tissue responses of equal amplitudes. Consistent with the results presented in FIG. 19, this two-step positive portion of the biphasic shock waveform 164 theoretically requires a 15.6% lower leading-edge voltage than its one-step counterpart 154, which translates into a 28.8% reduction in required stored energy, and a potentially lower pain waveform for the patient since the leading edge of the shocking pulse is reduced.

Figure 21:
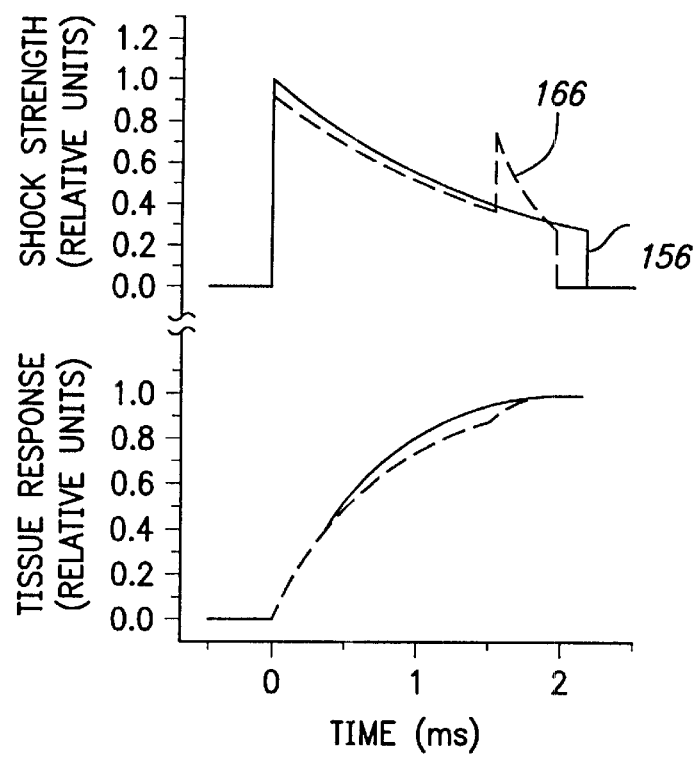
FIGS. 21 and 22 illustrate analogous results to those depicted in FIG. 20 albeit for extreme combinations of $R_S$ and $C_A$ ($=C_B$).
Figure 22:
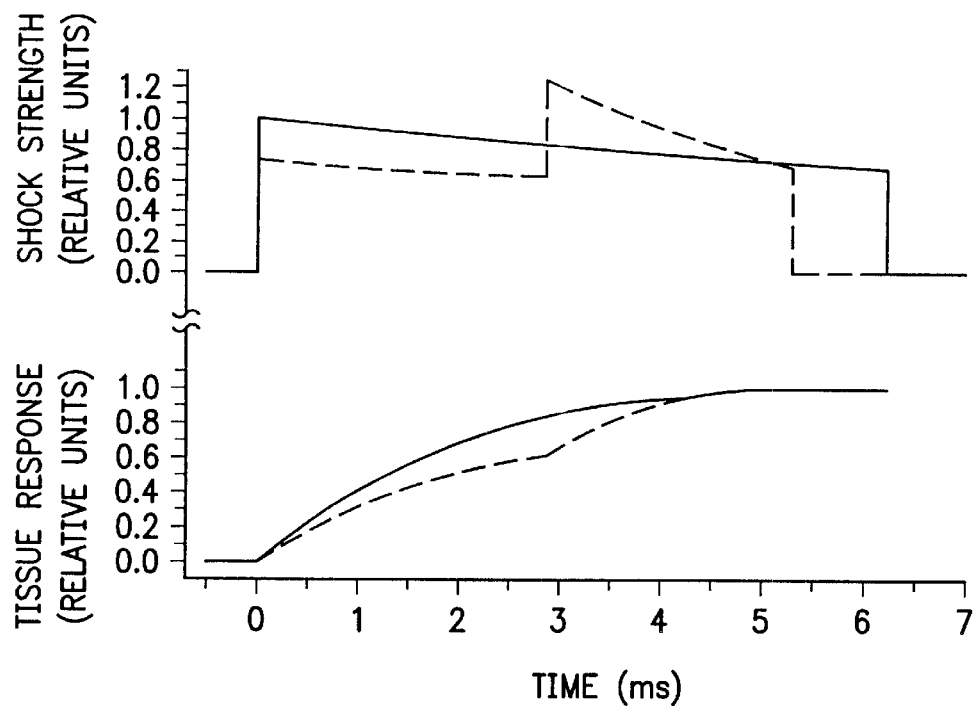

FIGS. 21 and 22 illustrate analogous results to those depicted in FIG. 20, but for relatively extreme combinations of $R_s$ and $C_A$. In FIG. 21, $R_s$=30 Ω and $C_A=C_B$=30 μF, while in FIG. 22, $R_s$=90 Ω and $C_A=C_B$=90 μF. As is evident in FIGS. 21 and 22, the shape of the optimal parallel-series two-step waveform depends strongly on the magnitudes of $R_s$ and $C_A$. Furthermore, the relative improvement in energy efficiency also strongly depends on these values.

For example, in FIG. 21, the two-step waveform 166 induced an equivalent final tissue response as its one-step waveform 156, but with an 8.8% shorter duration (2.1 vs. 2.3 ms), a 6.5% lower leading-edge voltage, and a 12.6% reduction in required stored energy.

In FIG. 22, the relative improvements were a 14.3% shorter duration (5.3 vs. 6.3 ms), a 25.9% lower leading-edge voltage, and a 45.0% reduction in required stored energy. Thus, these comparisons suggest that there would be especially great incentive for utilizing two-step waveforms instead of traditional one-step waveforms when the magnitudes of $R_s$ and $C_A$ are large, while the incentive is relatively minimal when the magnitudes of $R_s$ and $C_A$ are small. Unfortunately, because of the inherent limitations of this theoretical model, it is not possible to directly compare amplitude-based results (e.g., leading-edge voltage, required stored energy) derived for differing $R_s$ or $\tau_m$. For this reason, the results of FIGS. 20–22 are all self-normalized (that is, there is no relationship between the amplitudes in these graphs).

Finally, while Equations (16) and (17) provide exact formulas for determining $d_1^{opt}$ and $d_2^{opt}$ when k=1 (i.e., $C_A=C_B$), it is sometimes helpful and/or practical to also identify various approximations to such solutions. Consider the following infinite series expansion of the natural logarithm:

$$\ln[x] = 2 \cdot \left[\left(\frac{x-1}{x+1}\right) + \frac{1}{3} \cdot \left(\frac{x-1}{x+1}\right)^3 + \frac{1}{5} \cdot \left(\frac{x-1}{x+1}\right)^5 + \ldots \right] \quad (23)$$

Utilizing just the first term of this expansion, Equations (16) and (17) can be simplified to:

$$d_1^{opt} \approx \frac{2\tau_m}{3-\alpha_1} = \frac{2\tau_{s1} \cdot \tau_m}{2\tau_{s1}+\tau_m} \Rightarrow \frac{1}{d_1^{opt}} \approx \frac{1}{2\tau_{s1}} + \frac{1}{\tau_m} = \frac{1}{4R_sC_A} + \frac{1}{\tau_m} \quad (24)$$

$$d_2^{opt} \approx \frac{2\tau_m}{3-2\alpha_2} = \frac{\tau_{s2} \cdot 2\tau_m}{\tau_{s2}+2\tau_m} \Rightarrow \frac{1}{d_2^{opt}} \approx \frac{1}{\tau_{s2}} + \frac{1}{2\tau_m} = \frac{1}{2} \cdot \left(\frac{4}{R_sC_A} + \frac{1}{\tau_m}\right) \quad (25)$$

In words, these relationships suggest that the optimal step durations can be well approximated by computing variously weighted parallel combinations of system and myocardial time constants. And despite using only one term of Equation (23), these approximations are relatively quite accurate over a broad range of $\tau_{s1}/\tau_m$ and $\tau_{s2}/\tau_m$ ratios (only their ratios, not their absolute values, impact their accuracy). For example, the relative error for $d_1^{opt}$ is less than 5% for $0.4<\tau_{s1}/\tau_m<5$, while the relative error for $d_2^{opt}$ is less than 5% for $0.2<\tau_{s2}/\tau_m<3$. When Equation (20) is also satisfied (that is, when system and myocardial time constants are ideally matched), these relative errors are each only 1.35%. In all cases, these approximation calculations underestimate the true values by these respective relative errors.

While the invention herein disclosed has been described by means of specific embodiments and applications thereof, numerous modifications and variations could be made thereto by those skilled in the art without departing from the scope of the invention set forth in the claims.

What is claimed is:

1. A method for generating an improved biphasic defibrillation waveform, comprising the steps of:
   charging at least two capacitors to a first voltage;
   switchably coupling the at least two capacitors to a patient's heart in one of a parallel, a series or a parallel/series combination configuration;
   generating a biphasic shocking pulse having a positive phase and a negative phase, the positive phase having a first portion with a first peak voltage followed by a first time interval and at least a second portion with second peak voltage followed by at least a second time interval before being truncated and beginning the negative phase, the sum of the first and at least the second time intervals defining a desired pulse width; and
   determining an optimum duration for each time interval based on a maximum myocardial cell membrane potential produced in response to each portion of the positive phase so that, for the desired pulse width, the shocking pulse produces a higher final cell membrane potential than a value that would be achieved if the at least two capacitors were continuously discharged in series.

2. The method of claim 1, wherein the step of determining the optimum duration for each time interval comprises the step of:
   determining the optimum durations for each time interval based on the value of the at least two capacitors, a predetermined tissue time constant, $\tau_m$, and a predetermined tissue resistance, $R_S$.

3. The method of claim 2, further comprising the steps of:
   connecting the at least two capacitors in parallel during the first time interval of the biphasic shocking pulse; and
   connecting the at least two capacitors in series during at least the second time interval of the biphasic shocking pulse.

4. The method of claim 3, wherein the at least two capacitors includes a first capacitor, $C_A$, and a second capacitor, $C_B$, the method further comprising the steps of:
   generating, during the first portion of shocking pulse, a waveform having an exponential decay defined by a first time constant, $\tau_{s1}$, that varies as a function of the predetermined tissue resistance, $R_S$, and the first and second capacitors, $C_A$ and $C_B$, in accordance with the formula $R_S(C_A+C_B)$; and
   generating, during the second portion of shocking pulse, a waveform having an exponential decay defined by a second time constant, $\tau_{s2}$, that varies as a function of the predetermined tissue resistance, $R_S$, and the first and second capacitors, $C_A$ and $C_B$, in accordance with the formula $R_S(C_A \cdot C_B)/(C_A+C_B)$.

5. The method of claim 4, wherein:
   the step of determining the optimum duration, $d_1^{opt}$, for the first time interval comprises the step of defining:

$$d_1^{opt} = -\frac{\tau_m}{\alpha_1} \cdot \ln\left\{\left(\frac{\tau_m}{\tau_{s1}}\right)\left(\frac{2\alpha_1 - \alpha_2}{\alpha_1 - \alpha_2}\right)\right\}$$

the step of determining the optimum duration, $d_2^{opt}$, for the second time interval comprises the step of defining:

$$d_2^{opt} = +\frac{\tau_m}{\alpha_2} \cdot \ln\left\{\left(\frac{1}{2}\right)\left(\frac{2\alpha_1 - \alpha_2}{\alpha_1 - \alpha_2}\right)\right\}$$

wherein $\alpha_1=1-(\tau_m/\tau_{s1})$ and $\alpha_2=1-(\tau_m/\tau_{s2})$; and
wherein $\tau_{s1}=R_S \cdot (C_A+C_B)$ and $\tau_{s2}=R_S \cdot (C_A C_B)/(C_A+C_B)$.

6. The method of claim 5, wherein the step of determining the optimum duration for each time interval comprises the step of:
   determining the optimum value for the first and second capacitors, $C_A$ and $C_B$, that maximizes the final myocardial cell membrane potential for a given total stored energy.

7. The method of claim 6, wherein the first and second capacitors, $C_A$ and $C_B$, are related by a scaling factor defined by a relationship $k=C_A/C_B$, wherein the step of determining the optimum values for the first and second capacitors, $C_A$ and $C_B$, comprises the step of:
   defining a range for the scaling factor, k, as being approximately within the range of $0.7<k<1.4$ so as to be within approximately 1% of an optimal energy efficiency for a given $\tau_m$ and $R_S$.

8. The method of claim 7, wherein the step of determining the optimum values for the first and second capacitors, $C_A$ and $C_B$, comprises the step of:
   defining the value for capacitor, $C_A$, approximately equal to the value for capacitor, $C_B$.

9. The method of claim 8, wherein the step of determining the optimum duration for each time interval comprises the step of:
   defining the relationship between the first time constant, $\tau_{s1}$, and the second time constant, $\tau_{s2}$, as $\tau_{s1}=4 \cdot \tau_{s2}$.

10. The method of claim 9, wherein the step of determining the optimum values for the first and second capacitors, $C_A$ and $C_B$, comprises the step of:
   determining the optimum value for the first and second capacitors, $C_A$ and $C_B$, that minimizes the total stored energy needed for the predetermined tissue time constant, $\tau_m$ and the predetermined tissue resistance, $R_S$.

11. The method of claim 10, wherein the step of determining the optimum values for the first and second capacitors, $C_A$ and $C_B$, comprises the step of:
   defining a relationship between $C_A+C_B$ and $\tau_m/R_S$ in accordance with the following approximate range:

$$1.5 \cdot \tau_m/R_S < (C_A+C_B) < 2.7 \cdot \tau_m/R_S$$

so as to be within approximately 1% of optimal energy efficiency for a given $\tau_m$ and $R_S$.

12. The method of claim 11, wherein the step of determining the optimum values for the first and second capacitors, $C_A$ and $C_B$, comprises the step of:
   defining a relationship between $C_A$, $C_B$ and $\tau_m/R_S$ in accordance with the formula:

$$C_A=C_B=\tau_m/R_S$$

so as to result in the minimum total stored energy needed for a given $\tau_m$ and $R_S$.

13. The method of claim 12, wherein the step of determining the optimum values for the first and second capacitors, $C_A$ and $C_B$, comprises the step of:

defining the relationship between the first time constant, $\tau_{S1}$, and the second time constant, $\tau_{S2}$, and the predetermined tissue time constant, $\tau_m$, by the formula $\frac{1}{2}\tau_{S1}=2\cdot\tau_{S2}=\tau_m$.

14. The method of claim 12, wherein the step of determining the optimum duration for each time interval comprises the steps of:

defining the optimal duration for the first time interval as being approximated by the formula:

$$d_1^{opt}=0.811\cdot\tau_m;\text{ and}$$

defining the optimal duration for the second time interval as being approximated by the formula:

$$d_2^{opt}=0.405\cdot\tau_m.$$

15. The method of claim 13, wherein the step of determining the optimum duration for each time interval comprises the steps of:

defining the optimum value for $C_A$ and $C_B$ approximately equal to 60 $\mu$F each;

defining an approximate range of 2–4 ms over which the tissue time constant, $\tau_m$, may vary for any given patient;

defining an approximate range of 30–90 ohms over which the tissue resistance, $R_S$, may vary for any given patient;

defining an approximate range of 1.5 ms–3.5 ms for the optimal duration of the first time interval; and defining an approximate range of 0.7 ms–2.1 ms for the optimal duration of the second time interval.

16. The method of claim 2, wherein the step of determining the optimum duration for each time interval comprises the step of:

programming an approximate value for the predeteremined tissue time constant, $\tau_m$.

17. The method of claim 2, wherein the step of determining the optimum duration for each time interval comprises the step of:

programming an approximate value for the predetermined tissue resistance, $R_S$.

18. The method of claim 2, wherein the step of determining the optimum duration for each time interval comprises the step of:

measuring the tissue resistance, $R_S$.

* * * * *